US00PP25816P2

(12) United States Plant Patent
Wain

(10) Patent No.: US PP25,816 P2
(45) Date of Patent: Aug. 18, 2015

(54) ***CHRYSANTHEMUM* PLANT NAMED 'FIMMDAYBRIYEL'**

(50) Latin Name: *Chrysanthemum×morifolium*
Varietal Denomination: Fimmdaybriyel

(71) Applicant: Peter Wain, Locks Heath (GB)

(72) Inventor: Peter Wain, Locks Heath (GB)

(73) Assignee: Fides B.V., De Lier (NL)

( * ) Notice: Subject to any disclaimer, the term of this patent is extended or adjusted under 35 U.S.C. 154(b) by 178 days.

(21) Appl. No.: 13/987,342

(22) Filed: Jul. 15, 2013

(51) Int. Cl.
*A01H 5/00* (2006.01)

(52) U.S. Cl.
USPC ..... Plt./289

(58) Field of Classification Search
USPC ..... Plt./289
See application file for complete search history.

*Primary Examiner* — Annette Para
(74) *Attorney, Agent, or Firm* — C. A. Whealy

(57) ABSTRACT

A new and distinct cultivar of *Chrysanthemum* plant named 'Fimmdaybriyel', characterized by its upright to outwardly spreading and uniformly mounded plant habit; freely branching habit; dense and full plant habit; uniform and freely flowering habit; medium-size decorative-type inflorescences with deep yellow-colored ray florets; early flowering habit; and good garden performance.

1 Drawing Sheet

Botanical designation: *Chrysanthemum×morifolium.*
Cultivar denomination: 'FIMMDAYBRIYEL'.

BACKGROUND OF THE INVENTION

The present invention relates to a new and distinct *Chrysanthemum* plant, botanically known as *Chrysanthemum×morifolium,* commercially grown as a garden *Chrysanthemum* and hereinafter referred to by the name 'Fimmdaybriyel'.

The new *Chrysanthemum* plant is a product of a planned breeding program conducted by the Inventor in Fareham, Hampshire, United Kingdom. The objective of the breeding program is to create new early-flowering garden *Chrysanthemum* plants with numerous attractive inflorescences.

The new *Chrysanthemum* plant originated from a cross-pollination made in January, 2008 by the Inventor in Fareham, Hampshire, United Kingdom of a proprietary selection of *Chrysanthemum×morifolium* identified as code number 83322, not patented, as the female, or seed, parent with a proprietary selection of *Chrysanthemum×morifolium* identified as code number 83309, not patented, as the male, or pollen, parent. The new *Chrysanthemum* plant was discovered and selected by the Inventor as a single flowering plant from within the progeny of the stated cross-pollination in a controlled greenhouse environment in Fareham, Hampshire, United Kingdom in September, 2008.

Asexual reproduction of the new *Chrysanthemum* by terminal vegetative cuttings was first conducted in Fareham, Hampshire, United Kingdom in December, 2008. Asexual reproduction by terminal vegetative cuttings has shown that the unique features of this new *Chrysanthemum* are stable and reproduced true to type in successive generations.

SUMMARY OF THE INVENTION

Plants of the new *Chrysanthemum* have not been observed under all possible environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Fimmdaybriyel'. These characteristics in combination distinguish 'Fimmdaybriyel' as a new and distinct *Chrysanthemum* plant:

1. Upright to outwardly spreading and uniformly mounded plant habit.
2. Freely branching habit; dense and full plant habit.
3. Uniform and freely flowering habit.
4. Medium-size decorative-type inflorescences with deep yellow-colored ray florets.
5. Early flowering habit, under natural season conditions, plants flower the third week in August in the United Kingdom.
6. Good garden performance.

Plants of the new *Chrysanthemum* can be compared to plants of the female parent selection. Plants of the new *Chrysanthemum* differ from plants of the female parent selection, in the following characteristics:

1. Under natural season conditions, plants of the new *Chrysanthemum* flower earlier than plants of the female parent selection.
2. Plants of the new *Chrysanthemum* have larger inflorescences than plants of the female parent selection.

Plants of the new *Chrysanthemum* can be compared to plants of the male parent selection. Plants of the new *Chrysanthemum* differ from plants of the male parent selection, in the following characteristics:

1. Plants of the new *Chrysanthemum* have slightly smaller inflorescences than plants of the male parent selection.
2. Plants of the new *Chrysanthemum* and the male parent selection differ in ray floret color as plants of the male parent selection have lighter yellow-colored ray florets.

Plants of the new *Chrysanthemum* can be compared to plants of *Chrysanthemum×morifolium* 'Syngigi Yellow', disclosed in U.S. Plant Pat. No. 22,514. In side-by-side comparisons conducted in Fareham, Hampshire, United Kingdom, plants of the new *Chrysanthemum* differed from plants of 'Syngigi Yellow' in the following characteristics:

1. Under natural season conditions, plants of the new *Chrysanthemum* flowered earlier than plants of 'Syngigi Yellow'.
2. Plants of the new *Chrysanthemum* had larger inflorescences than plants of 'Syngigi Yellow'.
3. Plants of the new *Chrysanthemum* and 'Syngigi Yellow' differed slightly in ray floret color.

BRIEF DESCRIPTION OF THE PHOTOGRAPH

The accompanying photograph illustrates the overall appearance of the new *Chrysanthemum* showing the colors as true as it is reasonably possible to obtain in colored reproductions of this type. Colors in the photograph may differ slightly from the color values cited in the detailed botanical description which accurately describe the colors of the new *Chrysanthemum.*

The photograph comprises a top perspective view of a typical flowering plant of 'Fimmdaybriyel' grown in a container.

DETAILED BOTANICAL DESCRIPTION

The aforementioned photograph and following observations and measurements describe plants grown during the winter in 14-cm containers in a glass-covered greenhouse in Fareham, Hampshire, United Kingdom and under cultural practices typical of commercial garden *Chrysanthemum* production. During the production of the plants, day and night temperatures ranged from 17° C. to 21° C. and light levels averaged 6,000 lux. Plants were pinched one time and were about twelve weeks old when the photograph and detailed description were taken. In the following description, color references are made to The Royal Horticultural Society Colour Chart, Fifth Edition, except where general terms of ordinary dictionary significance are used.

Botanical classification: *Chrysanthemum×morifolium* 'Fimmdaybriyel'.

Parentage:

*Female, or seed, parent.*—Proprietary selection of *Chrysanthemum×morifolium* identified as code number 83322, not patented.

*Male, or pollen, parent.*—Proprietary selection of *Chrysanthemum×morifolium* identified as code number 83309, not patented.

Propagation:

*Type.*—Terminal vegetative cuttings.

*Time to initiate roots, summer.*—About ten days at temperatures of about 21° C.

*Time to initiate roots, winter.*—About twelve days at temperatures of about 21° C.

*Time to produce a rooted young plant, summer.*—About three weeks at temperatures of about 21° C.

*Time to produce a rooted young plant, winter.*—About four weeks at temperatures of about 21° C.

*Root description.*—Fine, fibrous; light brown in color.

*Rooting habit.*—Freely branching; medium density.

Plant description:

*Plant and growth habit.*—Herbaceous decorative-type garden *Chrysanthemum;* stems upright to outwardly spreading giving a uniformly mounded appearance to the plant; numerous lateral branches and relatively short internodes, dense and full plant habit; moderately vigorous growth habit.

*Plant height.*—About 11 cm.

*Plant width.*—About 24.5 cm.

*Branching habit.*—Freely branching habit, about six lateral branches develop after removal of terminal apex (pinching); each primary lateral with numerous secondary and tertiary lateral branches.

*Lateral branches.*—Length: About 7.5 cm. Diameter: About 3 mm. Internode length: About 5 mm. Strength: Strong, brittle. Aspect: About 70° from stem bending upwardly. Texture: Fine pubescence. Color: Close to 146D.

*Leaves.*—Arrangement: Alternate, simple. Length: About 6.5 cm. Width: About 5 cm. Shape: Palmately-lobed; roughly ovate with three to five lobes. Apex: Mucronate to acuminate. Base: Obtuse or truncate with attenuate tendencies. Margin: Palmately lobed, sinuses between lateral lobes parallel to divergent; dentate. Texture, upper and lower surfaces: Fine pubescence; veins prominent on lower surface. Color: Developing leaves, upper surface: Close to 137B. Developing leaves, lower surface: Close to 138B. Fully expanded leaves, upper surface: Close to 137A; venation, close to 137C. Fully expanded leaves, lower surface: Close to 147B; venation, close to 147C. Petioles: Length: About 2 cm. Diameter: About 3 mm. Texture, upper and lower surfaces: Fine pubescence. Color, upper surface: Close to 137C. Color, lower surface: Close to 147B.

Inflorescence description:

*Form and flowering habit.*—Decorative-type inflorescence form with ligulate-shaped ray florets; inflorescences borne on terminals above and beyond the foliar plane; disc and ray florets arranged acropetally on a capitulum; freely flowering habit with 72 inflorescences developing per plant.

*Fragrance.*—Mildly fragrant; pungent, herbaceous.

*Flowering response.*—Early flowering habit, plants exposed to natural season conditions begin flowering the third week of August in the United Kingdom.

*Inflorescence longevity.*—Inflorescences maintain good color and substance for about three to five weeks on the plant; inflorescences persistent.

*Inflorescence buds.*—Height: About 5 mm. Diameter: About 6 mm. Shape: Oblate. Color: Close to 145B.

*Inflorescence height.*—About 1.5 cm.

*Inflorescence diameter.*—About 5 cm.

*Receptacles.*—Height: About 2 mm. Diameter: About 3 mm. Shape: Hemispherical to nearly spherical. Color: Close to 145C.

*Ray florets.*—Orientation: Initially upright, then about 90° from vertical. Length: About 2.3 cm. Width: About 6 mm. Shape: Ligulate. Apex: Slightly emarginate or acute to rounded. Base: Fused into a short tube. Margin: Entire. Texture, upper and lower surfaces: Smooth, glabrous. Number of ray florets per inflorescence: About 145 arranged in about nine whorls. Color: When opening, upper surface: Close to 9A. When opening, lower surface: Close to 6C. Fully opened, upper surface: Close to 9B; color becoming closer to 9C with development. Fully opened, lower surface: Close to 8B; color becoming closer to 8C with development.

*Disc florets.*—Disc floret development has not been observed on plants of the new *Chrysanthemum.*

*Phyllaries.*—Number of phyllaries per inflorescence: About 20 arranged in about four whorls. Length: About 6 mm. Width: About 2 mm. Shape: Lanceolate. Apex: Acute to obtuse. Base: Truncate, fused. Margin: Entire. Texture, upper surface: Smooth, glabrous. Texture, lower surface: Fine pubescence. Color, upper surface: Close to 144B. Color, lower surface: Close to 139B.

*Peduncles.*—Length, terminal peduncle: About 2.3 cm. Diameter, terminal peduncle: About 2 mm. Angle: About 20° from vertical. Strength: Moderately strong; flexible. Texture: Fine pubescence. Color: Close to 138C.

*Reproductive organs.*—Androecium: None observed. Gynoecium: Pistil length: About 4 mm. Stigma shape: Bi-parted. Stigma color: Close to 12B. Style length: About 2 mm. Style color: Close to 1B. Ovary color: Close to 157C.

*Seeds and fruits.*—Seed and fruit production has not been observed on plants of the new *Chrysanthemum.*

Disease & pest resistance: Resistance to pathogens and pests common to *Chrysanthemum* plants has not been observed on plants of the new *Chrysanthemum.*

Garden performance: Plants of the new *Chrysanthemum* have demonstrated good garden performance and to tolerate temperatures from about 0° C. to about 35° C.

It is claimed:

1. A new and distinct *Chrysanthemum* plant named 'Fimmdaybriyel' as illustrated and described.

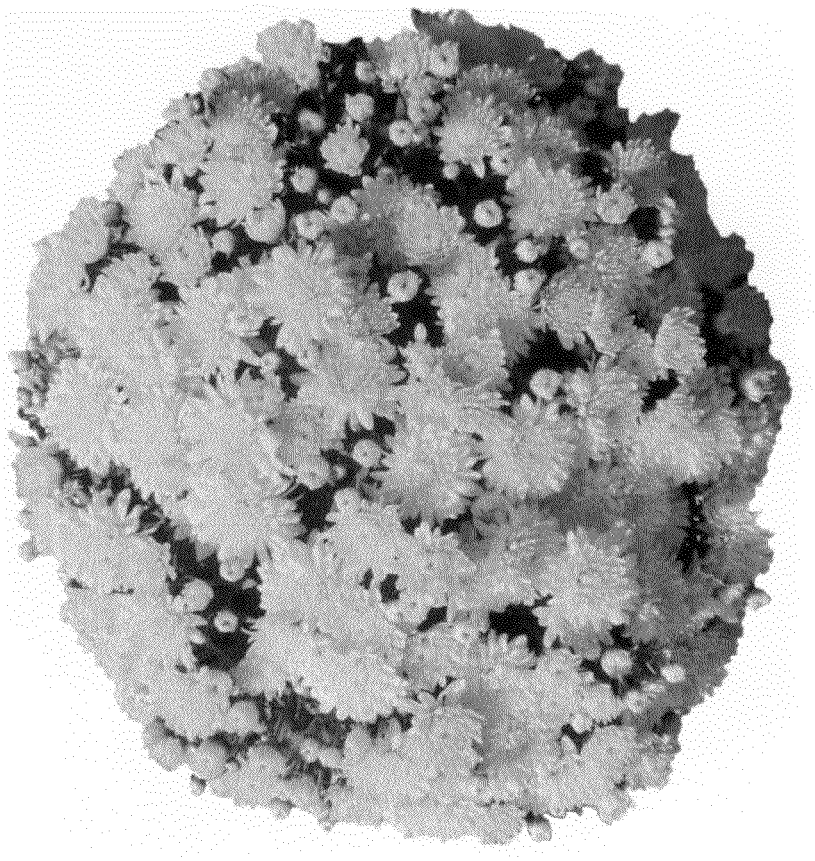

* * * * *